United States Patent [19]

Semoff et al.

[11] Patent Number: 6,071,506

[45] Date of Patent: *Jun. 6, 2000

[54] GEL FRESHENER AND METHOD OF MAKING THE SAME

[75] Inventors: Steven Semoff, Nyack, N.Y.; Rueven Sarraf, Teaneck, N.J.

[73] Assignee: Bath & Body Works, Inc., Columbus, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/883,024

[22] Filed: Jun. 26, 1997

Related U.S. Application Data

[62] Division of application No. 08/696,493, Aug. 14, 1996, Pat. No. 5,679,334.

[51] Int. Cl.[7] ........................................................ A61L 9/04
[52] U.S. Cl. ......................................... 424/76.4; 424/76.3
[58] Field of Search ............................................ 424/76.4

[56] References Cited

U.S. PATENT DOCUMENTS

| | | | |
|---|---|---|---|
| 4,876,105 | 10/1989 | Wolf et al. | 426/573 |
| 5,034,222 | 7/1991 | Kellett et al. | 426/76.4 |
| 5,549,921 | 8/1996 | Robinson et al. | 426/573 |
| 5,679,334 | 10/1997 | Semoff et al. | 424/76.4 |
| 5,741,482 | 4/1998 | Moni | 424/76.4 |

FOREIGN PATENT DOCUMENTS

| | | | |
|---|---|---|---|
| 62-152466 | 7/1987 | Japan | 424/76.4 |
| 219162 | 7/1988 | Japan . | |
| 6427560 | 1/1989 | Japan | 424/76.4 |
| 2012162 | 2/1990 | Japan | 424/76.4 |

*Primary Examiner*—Peter F. Kulkosky
*Attorney, Agent, or Firm*—Colucci & Umans

[57] ABSTRACT

A transparent gel air freshener and method of preparing the same. The gel composition comprises an aqueous gel, a fragrance, a surfactant and a co-solvent. The gel is transparent and free from visible particles and inhomogeneities, has a uniform texture and a continuous structure, and includes volatile scented components. The gel is capable of suspending solids such as botanicals therein for decorative effect. The method provides for preparation of a such a gel air freshener, including the suspension of botanicals therein, while maintaining the clarity, texture, and structure of the gel. The method includes the steps of preparing a gel composition and cooling the gel composition. Botanicals may be added to the gel composition when it has gelled enough to support the botanicals on the gel surface.

6 Claims, No Drawings

GEL FRESHENER AND METHOD OF MAKING THE SAME

This application is a division of application Ser. No. 08/696,493, filed Aug. 14, 1996, now U.S. Pat. No. 5,679, 334.

BACKGROUND AND SUMMARY OF THE INVENTION

This invention relates generally to a gel composition suitable for use as an air freshener, and particularly a decorative transparent gel composition having one or more solid articles suspended therein.

Compositions which release fragrant volatile components into the air have long been used as air fresheners. Traditionally, such compositions have been valued for their utilitarian ability to impart a desired scent into the air and mask stale or unpleasant odors. Within the household, they have found their greatest use in areas where stale or unpleasant odors are most likely to occur, such as bathrooms and kitchens. The containers or dispensers used to disperse these compositions into the air have tended to be more functional than attractive, despite efforts to the contrary.

More recently, scent-releasing compositions have come to be used to extend a room's decor or theme into an additional sensory dimension or to evoke a particular feeling or mood. For example, the scent of aromatic woods may be used to bring the feeling of the outdoors into the home, or a spicy apple scent may be used to induce nostalgic recollections of home-baked pies. The scents used in these compositions typically are more complex and sophisticated than the heavily perfumed, disinfectant-type scents commonly used in traditional air freshening compositions.

The trend toward the use of scented compositions to enhance home decor and ambiance has resulted in increased use of these scented compositions in areas of the household, such as bedrooms and living rooms, where traditional air fresheners are less frequently used. Persons who wish to use scented compositions in these areas of the home, however, may be reluctant to place an unattractive, functional container in these areas of the home. Thus, a need exists for a scented composition that may be packaged in an aesthetically pleasing container that harmonizes with, or even enhances, household decor.

Air fresheners have been prepared in the form of pastes or gels to control spills or leaks. These pastes and gels generally have had a nonuniform appearance, with breaks or discontinuities in their structure or texture that detract from the appearance of these compositions. These discontinuities are particularly noticeable when the compositions are packaged in transparent containers. In addition, these air freshening pastes and gels have tended to have a cloudy or opaque appearance resulting from the phase separation of the aqueous base components and the oil-based fragrance components. The cloudy appearance of these compositions makes them undesirable for decorative use, particularly when they are packaged in transparent containers. The phase separation problem becomes increasingly difficult to solve when a relatively high fragrance concentration is used in the gel composition. It is sometimes possible to increase the surfactant level in the composition to reduce or eliminate the phase separation. However, this approach often is ineffective because the higher surfactant level adversely affects the fragrance-dispersing capability of the composition.

Because scented compositions are finding greater use in living areas of the home where their appearance is important, it may be desirable to place solids within the body of a transparent gel, and particularly within a specific region of the gel, to achieve a decorative effect. However, these solids generally will tend to float or sink depending on their specific gravity, resulting in an unattractive clumping of the solids at the top or bottom of the gel. This problem is compounded when the gel is intended to be displayed for decorative purposes in a transparent container, because the suspension of the solids in a specific region of the gel must be accomplished without fracturing or otherwise disrupting the desired smooth and uniform appearance of the gel.

In keeping with the increased emphasis on the natural environment and nostalgic themes, the solids desired to be dispersed throughout the gel may be botanical specimens, such as berries, slices of fruit, leaves, seeds, flowers, herbaceous sprigs, small branchlets and the like. These natural substances may be adversely affected by the moisture or other substances present in the gel. Swelling from absorption of water, bleeding of color into the gel, leakage of fluids from the botanicals into the gel and other types of unsightly deterioration have been observed in botanicals that have been immersed in a transparent gel. These adverse effects may limit the use of botanicals in decorative gel air fresheners.

SUMMARY OF THE INVENTION

In light of the disadvantages of the prior art, a composition is needed that will provide a strong, transparent, shiny gel including a volatile component that will evaporate over a predetermined period of time to impart a desired fragrance to the surrounding environment. The volatile constituents of the gel may evaporate, under typical household conditions, over a period from about two weeks to about three months, and particularly from about twenty to about forty-five days, with the most desired period being about thirty days. When the fragrance has been depleted, the user may replace it with another gel having the same scent select a differently-scented gel to mark the change of seasons, a holiday or other event, or set a different mood. Preferably, the fragrance is distributed substantially uniformly within the gel composition to assist in dispersion of the fragrance into the air at the desired rate. More importantly, the fragrance constituents are selected to that the perceived fragrance dispersed into the air remains consistent during the desired period of use, without any untoward diminution of the perceived strength or quality of the fragrance over time.

The gel must possess a uniform and pleasing appearance when packaged in a transparent container. Thus, the gel must be transparent and free from particles or inhomogeneities, such as oil droplets, that are apparent upon visual inspection. It also must possess a uniform texture and a continuous structure. The ideal gel will have a shiny, elegant appearance. The gel may be colored, if desired, with any of a variety of nontoxic coloring agents to enhance its decorative effect.

Further, the gel composition must possess low toxicity and flammability such that it is suitable for household use. A preservative or microbiocide may be added to the gel composition to discourage growth of microorganisms that can adversely affect the appearance or fragrance of the gel. An aversive agent also may be present to discourage accidental ingestion of the gel.

The gel may be capable of suspending a variety of solids therein to create a decorative effect. When the solids to be suspended are botanicals, the botanicals must retain their natural appearance even after immersion in the gel preparation.

Accordingly, it is an object of the present invention to provide a gel composition, and a method of preparing the same, suitable for use as a decorative household fragrance source or air freshener. The resultant gel is homogenous and transparent in appearance and possesses a uniform and continuous texture. The gel composition includes fragrant volatile components distributed substantially uniformly throughout the composition and capable of evaporating over a predetermined period of time to impart a desired fragrance to the surrounding environment.

Another object of the present invention is to provide a gel composition and method of making the same in which the resultant gel is capable of suspending a variety of solids therein, and particularly solids in the form of botanicals that retain a natural and attractive appearance even after immersion in the gel composition. 4 The foregoing objectives are achieved in a transparent gel composition including a water-soluble gelling agent, a fragrance, a surfactant and a cosolvent. The gel composition may be prepared by a method that includes the steps of preparing a gel mixture comprising the foregoing components and cooling the gel mixture to a temperature of about 38° C. to about 40° C. Botanicals may be added to the gel mixture before it is cooled completely.

These and further objects of the invention will become apparent from the following detailed description.

DETAILED DESCRIPTION OF THE PREFERRED EMBODIMENT(S)

The above objectives may be achieved in a transparent gel composition and method of making the same. The composition comprises an aqueous gel, a fragrance, a surfactant and a cosolvent. The aqueous gel includes a gelling agent, such as a modified polysaccharide gum. Botanicals may be suspended in the gel composition for decorative effect.

The preferred gelling agent to achieve the desired transparent, shiny gel is a modified polysaccharide, for example, a muccopolysaccharide. The gelling agent is crosslinked in the presence of a cationic crosslinking agent. KelcoGel gellan gum has been used successfully as a gelling agent, although other gelling agents also may be used. Cationic crosslinking agents are preferred for optimum clarity and gel structure. Potassium citrate is the preferred crosslinking agent. Satisfactory results also may be achieved with the use of other cationic crosslinking agents such as water-soluble calcium citrate and magnesium chloride.

The gel composition possesses a suitably low toxicity and low flammability for its intended use in a household. In some embodiments of the present invention, the gel composition may resemble jelly or preserves, particularly if the composition has a fruity fragrance or pieces of fruit are suspended in the gel. In such instances, an aversive agent (i.e., a nontoxic substance with a bitter or otherwise unpleasant taste) may be added to discourage inadvertent consumption of the gel composition. Bitrex (dentantonium benzoate) is a preferred aversive agent.

Under some conditions, the gel composition may provide a suitable medium for the growth of microorganisms. The growth of such microorganisms in the gel typically would cause the gel to develop a sour odor. Mold growth also may appear on the surface of the gel. To discourage the growth of such organisms and maintain the pleasant fragrance of the gel, a suitable preservative or microbiocide also may be added to the gel composition. Kathon microbiocide (a combination of methylchoroisothiazolinone and methyl isothiazolinone) is preferred for convenience and clarity. Satisfactory results also may be achieved using potassium sorbate or sodium benroate.

The fragrance is selected so that its bright, effervescent "top notes" are balanced with the heart, or "middle notes." The vapor pressure of the fragrance at 20° C. preferably does not exceed 0.1 mm Hg. Preferably, specially denatured alcohol, such as alcohol 40-2, is added to enhance the fragrance top notes. The specially denatured alcohol, when present, also may assist in solvating the fragrance and maintaining the initial clarity of the gel composition. The alcohol concentration preferably is less that 3% by weight of the gel composition to assist in maintaining compliance with regulations concerning the emission of volatile organic compounds.

A cosolvent, such as dipropylene glycol, may be used to reduce the interfacial tension between the fragrance oil and water and to assist in the movement of the oil through the gel matrix. Thus, cosolvents tend to moderate the evaporation rate of the fragrance and assist in maintaining a consistent odor perception. Preferably, the cosolvent is water-soluble or at least has an affinity for water. In addition to dipropylene glycol, compounds such as diethyl phthalate, benzyl alcohol, benzyl benzoate, propylene glycol and glyceryl triacetate may be suitable as cosolvents to slow the evaporation rate of the fragrance. Dipropylene glycol is preferred because it assists it contributes to the clarity of the gel product. Compounds that may be suitable for use as cosolvents to enhance the evaporation rate of the fragrance include ethanol and isopropanol.

In addition, the fragrance is selected so that the perceived fragrance dispersed into the air remains consistent during the desired period of use, without any untoward diminution of the perceived intensity or quality of the fragrance over time. This may be accomplished, for example, by a combination of "headspace analysis" and supercritical fluid extraction techniques. Headspace analysis involves the quantitative and qualitative analysis of the air over fragranced gel compositions of varying ages to determine the olefactive differences between fresh and aged products. The fragrance may be adjusted to keep these olefactive differences within an acceptable range, thereby avoiding sour or "off" odors sometimes associated with aged products. Supercritical fluid extraction techniques involve the passing of high pressure carbon dioxide through fragranced gel compositions of varying ages to extract the fragrance from the gel. These extracts are analyzed by gas chromatography to determine the differences in the types and amounts of various fragrance components, and particularly volatile esters, present in the fresh and aged gels as a result of selective evaporation. Persons skilled in the art of fragrance formulation and modification can use the results of these analyses to adjust the fragrance constituents to achieve a result that satisfies consumer expectations.

The preferred surfactant is a nonionic, ethoxylated alkyl phenol such as Rohm & Haas Triton X-102. Nonionic surfactants are preferred because the provide the best clarity and highest activity. The surfactant should have a low odor and a high hydrophilic-lipophilic balance for optimum solubilizing of the fragrance oils. Satisfactory results also may be achieved using other nonionic surfactants, such as nonyl phenols and ethyoxylated alcohols, with similar properties.

The clarity of the gel product is a function of the amounts of fragrance and surfactant present in the gel composition. Thus, the type or amount of surfactant may require adjustment if the type or amount of fragrance is changed. In addition, when certain surfactants or combinations of surfactants are used with particular fragrances, the gel composition may become unstable as the temperature of the product is decreased. This instability typically is manifested by a clouding of the product as the temperature of the product passes below the "cloud point," indicating a breakdown of the oil-water microemulsion. As a result, it may be necessary to adjust the particular surfactant(s) with a particular fragrance to maintain this "cloud point" below a desired temperature.

The table immediately below sets forth illustrative and preferred weight percents of the components of the gel mixture used in the instant invention based on the total weight of the mixture:

| Component | Preferred Range | Illustrative Range |
|---|---|---|
| Deionized water | 79.56 | |
| Gelling agent | 0.80 | 0.05–10 |
| Crosslinking agent | 0.40 | 0.001–15 |
| Aversive agent | 0.05 | 0–0.1 |
| Coloring agents (1% in water) | 0.14 | 0–0.2 |
| Microbiocide/preservative | 0.05 | 0–0.1 |
| Nonionic surfactant | 6.0 | 0.5–20 |
| Fragrance | 5.0 | 0.1–15 |
| Dipropylene glycol | 5.0 | 0.1–30 |
| Alcohol 40-2 | 3.0 | 0–3 |

The gel composition prepared from the preferred components in the above-described categories results in a product having the desired attributes when used in conjunction with the process herein described. Suitable gels can be made with components of the gelling system used in amounts shown in the "preferred" range in the above table. However, the characteristics of the end product may be slightly modified from that obtained when the amounts used are in the "illustrative" range.

The method of the present invention includes the steps of:
A. Preparing a suitable liquified gel mixture; and
B. Chilling the gel mixture to a temperature of about 38° C. to about 40° C. The term "gel mixture" is used to describe an aqueous gel including a gelling agent such as sodium alginate or the like, a fragrance, a co-solvent and a surfactant. Botanicals may be suspended in the gel mixture before it cools completely and gels as described in more detail below.

The method of making the gel composition may vary to some extent depending on such factors as the particular constitutents used and whether the composition is being prepared in a laboratory or a commercial production facility. The description below generally reflects commercial production of the gel composition. Slightly different steps used in laboratory production of the gel composition are described in the Example.

The gel mixture may be prepared by dispersing a modified polysaccharide gum, such as KelcoGel gellan gum, in water. Best results are achieved when the water is at about room temperature. It also is possible to add the gellan gum to warm water, but this increases the likelihood of agglomeration of the gellan gum before it is completely hydrated.

The resultant dispersion is heated to about 75° C. with stirring or other agitation, preferably in a high shear mixer, until the dispersion becomes clear and the gel is completely hydrated. The crosslinking agent, and, if desired, the aversive agent and water-soluble coloring agents may be added to the water either before or after it is mixed with the gel. The dispersion is maintained at this temperature for about 5 to 10 minutes to allow complete dispersal of the gellan gum and ensure good crosslinking of the gum. Heating to lower temperatures and/or a shorter holding time may result in formation of a gel that is unacceptably soft.

A fragrance solution may be prepared by combining a surfactant, such as Rohm & Haas' Triton X-102 nonionic surfactant, a fragrance, a fragrance cosolvent such as dipropylene glycol, and, if desired, a microbiocide or preservative. The fragrance solution sometimes is referred to as the "oil phase," although all of its constituents except for the fragrance are water-soluble. These components are stirred or otherwise agitated, preferably for about 10 minutes, until the solution is clear. Preferably, specially denatured alcohol 40-2 is also added to the fragrance solution to enhance the pungency of the top note of the fragrance.

The gel mixture and the fragrance solution are combined and mixed for about 10 to 15 minutes while the temperature of the mixture is decreased to about 60° C. The mixture will be milky or opaque upon initial blending at temperatures greater than about 55° C., but will clear as the temperature approaches about 50° C., indicating that a microemulsion has been formed.

The gel mixture may be poured into suitable containers. This should be done while the mixture is warn to avoid congealing of the gel before the containers are filled. Use of fluted or textured containers will reduce the likelihood that striations or pores in the gel will be visible, although flat glass containers also may be used. The containers are cooled, for example, in an ice bath or a chilling unit such as a chill table. When the gel mixture has been chilled to a suitable temperature, typically about 38° C. to about 40° C., the mixture will attain the desired viscosity or gel structure. The gel will reliquify if the temperature in increased to about 60° C. or more.

If botanicals are to be added to the liquified gel, they may be positioned at a desired location within the gel by partially filling the gel container. Generally, the containers should be filled to about one third to three-fourths fill depending on the desired position of the botanicals in the container. The partially filled containers are cooled as described above, typically to about 38° C. to about 40° C., until the mixture attains a viscosity and/or weak gel structure capable of supporting botanicals or other solids placed on the gel surface, such that the botanicals will not tend to sink into the gel, but rather will be maintained in a desired position and level within the container. If the desired viscosity or gel structure is not achieved, however, any solids intended to be suspended in the gel may tend to float or sink depending on the specific gravity of the solids, resulting in an undesirable clumping of the solids in the top or bottom of the container.

The time required for the gel to develop sufficient viscosity to support botanicals on its surface will depend on the specific gravity of the botanicals relative to that of the gel. Less dense botanicals may be supported on a less viscous gel, but denser botanicals will require gel of a higher viscosity for adequate support. For example, dry, delicate flowerheads of Queen Anne's lace typically will require a lower viscosity, and therefore less chilling time, than moist, dense botanicals such as berries or sliced peaches. The chilling time required for the gel to support low density botanicals may be as short as about 10 to 15 seconds for a small, partially filled jar in an ice bath.

When the desired gel structure has been achieved, the botanicals may be added. Additional warm, liquified gel may be added until the container has been filled to the level desired and chilled until the added gel thickens. Care must be taken when adding additional liquified gel to avoid disturbing the desired arrangement of the botanicals or the continuous structure of the partially set gel layer. Preferably, the containers are allowed to cool to a temperature approaching room temperature. The containers may be handled normally without damage to the gel once the desired temperature is reached. However, extremely rough handling should be avoided to reduce the likelihood that the gel will pull way from the container walls.

Any packaging container of reasonable dimension can be employed for the gel preparation consistent with commercial custom. As described above, however, the container preferably is transparent to allow a viewer to perceive the texture and structure of the gel and the distribution of any solids suspended therein. Glass containers are preferred although other transparent container materials also may used to achieve the desired result.

As the container volume increases, the chilling time required to obtain the desired gel structure also increases. The maximum preferred container size is in the range of about 100 to 500 ml to promote effective cooling of the gel.

The botanicals may be selected so that they retain their natural appearance after they are immersed in the gel mixture. Botanicals containing water-soluble dyes or preservative are unsuitable for use as the dyes and preservatives tend to cause bleeding of the botanicals into the gel. This bleeding may be avoided by using botanicals without dyes or preservatives. The botanicals also may be bleached before they are added to the gel, either to remove natural color that may tend to bleed into the gel or to create a subtle, ethereal effect. Besides bleaching, the botanicals also may be treated, for example, by freeze-drying them or coating them with a moisture-resistant sealer before they are added to the gel mixture. The botanicals thus are or are made to be color-fast, which term is meant to include botanicals as described or as treated above.

EXAMPLE

A transparent yellow gel containing peach slices suspended therein was prepared in the laboratory as follows:

A. 79.56 weight percent deionized water, 0.4 weight percent potassium citrate and 0.05 weight percent Bitrex were combined with 0.09 weight percent FD&C Red #40 (1.0% in water), 0.03 weight percent D&C Red #33 (1.0% in water) and 0.02 eight percent FD&C Yellow #5 (1.0% in water). The resultant solution was mixed until it appeared clear.

B. 0.80 weight percent KelcoGel gellan gum was dispersed into the colored water solution, and the resulting dispersion heated to a temperature of about 75° C. with stirring until the dispersion became clear, then cooled to a temperature of about 60° C.

C. 0.05 weight percent Rohm & Haas Kathon was added to the aqueous gum dispersion with stirring until the mixture because clear, while maintaining the temperature of the mixture at about 60° C.;

D. A fragrance solution was prepared by combining 6.0 weight percent Rohm & Haas Triton X-102 surfactant, 5.0 weight percent fragrance oils, 3.0 weight percent alcohol 40-2 6 and 5.0 weight percent dipropylene glycol with stirring until the solution was clear.

E. The aqueous gum dispersion and the fragrance solution were mixed and blended until the mixture was uniform in appearance, avoiding air entrapment. The resultant mixture was 9 opaque upon initial blending at a temperature greater than about 55° C., but became clear as the temperature approached about 50° C.

F. The resultant mixture was poured into a container having a capacity of about one-fourth pint until the container was about ¾ full. The container was placed into a chilling unit to begin setting up the gel. When an acceptable level of gel viscosity was reached (e.g., upon reaching a at a temperature of about 38° C. to about 40° C.), about 10 grams sliced peaches were added. The balance of the container was then filled with liquified gel which was allowed to set.

The gel product typically is packaged in a sealed container with a removable lid. When the lid is removed, the volatile components of the gel evaporate and the fragrance is dispersed into the air over a period of time. The volatile constituents of the gel may evaporate over a period from about two weeks to about three months, and particularly from about twenty to about forty-five days, with the most desired period being about thirty days. The uniform distribution of the fragrance within the gel aids in dispersion of the fragrance into the air at the desired rate.

As the volatile components evaporate, the gel will shrink until, eventually, only a residue of essentially nonvolatile components will remain. The fragrance-dispersing capability of the composition will diminish as the proportion of volatile components decreases. The shrinkage of the gel therefore provides a user with an visual indication of when a new supply is needed.

Although a specific embodiment of the invention has been described herein in detail, it is understood that variations may be made thereto by those skilled in the art without departing from the spirit of the invention or the scope of the appended claims.

What is claimed is:

1. A method for making a transparent air freshener comprising the steps of:

mixing together about 0.001–15 wt % potassium citrate as a cross-linking agent, an aversive agent, about 0–0.2 wt % color and deionized water to form a first solution, the mixing step continuing until the first solution is clear;

dispersing into the first solution about 0.05–10 wt % modified polysaccaride gum as a gelling agent to form a dispersion;

heating the dispersion to above 60° C. and stirring the dispersion until the dispersion is clear;

after the dispersion is clear, cooling the dispersion to about 60° C.;

mixing together an initial mixture of about 0.5–20 wt % nonionic surfactant, about 0–3.0 wt % SD alcohol, about 0.1–30 wt % dipropylene glycol as a co-solvent and about 0.1–15 wt % fragrance until the initial mixture is clear;

mixing the initial mixture with the dispersion at a temperature greater than about 55° C. to form a resulting mixture and then cooling the resulting mixture until the resulting mixture becomes a clear mixture;

pouring the resulting mixture into a transparent container; and chilling the transparent container, said phase being free from clouding with resulting mixture to form a transparent, homogenous gel having one phase in the container;

the fragrance being present in an amount to provide a vapor pressure at 20° C. of not more than 0.1 mm Hg, the nonionic surfactant being in an amount to form the transparent gel having one phase, the co-solvent being in an amount to moderate evaporation of the fragrance so that the transparent gel acts to freshen a room by evaporation of the fragrance, said fragrance being released over a period of at least two weeks.

2. A method according to claim 1, including heating the dispersion to about 75° C.

3. A method according to claim 1, including chilling the resulting mixture to about 38–40° C.

4. A method according to claim 1, wherein the surfactant is Triton X-102.

5. A method according to claim 1, wherein the gelling agent is gellan gum.

6. A method according to claim 1 including partially filling the transparent container with the clear mixture; chilling the clear mixture to set the transparent gel; thereafter inserting the solids into the set gel; and thereafter adding additional clear mixture to cover the solids and complete the air freshener, the transparent gel appearing as one phase and suspending the solids in the one phase, without any separation being visible between the clear mixture portions added to the transparent container.

* * * * *